United States Patent [19]
Kolen et al.

[11] Patent Number: 5,865,841
[45] Date of Patent: Feb. 2, 1999

[54] COLD THERAPY APPARATUS

[76] Inventors: Paul T. Kolen, 139 Fourth St., Encinitas, Calif. 92024; Thomas D. Ford, 10405 Orozco St., San Diego, Calif. 92124

[21] Appl. No.: 450,641

[22] Filed: May 25, 1995

[30] Foreign Application Priority Data

Mar. 1, 1995 [IE] Ireland .................................. S950163

[51] Int. Cl.$^6$ .................................................. A61F 7/00
[52] U.S. Cl. .......................... 607/104; 607/114; 126/204
[58] Field of Search ............................ 607/104, 108–112, 607/114; 601/15, 148–152

[56] References Cited

U.S. PATENT DOCUMENTS

| | | | |
|---|---|---|---|
| 2,726,658 | 12/1955 | Chessey | 128/400 |
| 3,744,555 | 7/1973 | Fletcher et al. | 165/46 |
| 3,871,381 | 3/1975 | Roslonski | 128/400 |
| 3,993,053 | 11/1976 | Grossen | 607/104 |
| 3,995,621 | 12/1976 | Fletcher et al. | 607/104 |
| 4,026,299 | 5/1977 | Sauder | 128/400 |
| 4,149,529 | 4/1979 | Copeland et al. | 128/24.1 |
| 4,184,537 | 1/1980 | Sauder | 165/46 |
| 4,523,594 | 6/1985 | Kuznetz | 128/402 |
| 4,691,762 | 9/1987 | Elkins et al. | 165/46 |
| 4,821,354 | 4/1989 | Little | 5/422 |
| 4,844,072 | 7/1989 | French et al. | 607/104 |
| 5,051,562 | 9/1991 | Bailey et al. | 219/506 |
| 5,097,829 | 3/1992 | Quisenberry | 607/104 |
| 5,183,039 | 2/1993 | Sarian et al. | 607/104 |
| 5,241,951 | 9/1993 | Mason et al. | 607/104 |
| 5,330,519 | 7/1994 | Mason et al. | 607/104 |
| 5,476,489 | 12/1995 | Koewler | 607/114 |
| 5,486,207 | 1/1996 | Mahawili | 607/104 |
| 5,591,220 | 1/1997 | Mahawili | 607/104 |

FOREIGN PATENT DOCUMENTS 3343664  12/1983  Germany ................................ 607/104

OTHER PUBLICATIONS

"Electri–Cool Localized Cold Therapy System" (Seabrook Medical Systems, Inc., copyright 1991).
"Thermal–Max Hot and Cold Thermal Therapy" (Danniger Medical Technology, Inc.).
"The Standard in Thermal Therapy . . . " (Burke/Neutech, Inc.).
"The Thermal Therapy People" (Burke/Neutech Medical Systems).
"Cool–Aid Single–Patient Use Cold Therapy System" (Seabrook Medical Systems, Inc., copyright 1994).
"Polar Care Cold Therapy" (Breg, Inc., 2 pages).
Price list dated Sep. 1, 1994 (Breg, Inc.).

Primary Examiner—Robert L. Nasser
Attorney, Agent, or Firm—Fish & Richardson P.C.

[57] ABSTRACT

A thermal therapy apparatus for applying temperature controlled therapy to a therapy site on a mammalian body includes a therapy pad for applying a selected therapy temperature to the therapy site; a recirculating fluid loop, including a fluid channel defined by the therapy pad; a thermal reservoir; a heat exchanger coupling the thermal reservoir with the recirculating fluid loop, the heat exchanger including a pump for circulating fluid through the recirculating fluid loop; and a control mechanism coupled to the heat exchanger for enabling adjustable control of therapy temperature. The heat exchanger selectively mixes fluid recirculating in the fluid loop with fluid from the thermal reservoir in an adjustable mixing ratio to achieve the selected therapy temperature at the therapy site.

11 Claims, 4 Drawing Sheets

COLD THERAPY APPARATUS

BACKGROUND OF THE INVENTION

This invention relates to the application of cold or heat to affect heat transfer to or from the human or mammalian body. The necessity for such an application may arise in a wide range of circumstances. Most common are injuries, bruises, sprains, or other trauma to bone, muscle, ligaments, tendons, skin and other forms of mammalian tissue. The application of cold or cooling to reduce swelling, reduce pain and promote healing at the traumatized area of the human or mammalian body is often recommended. Similarly, the application of heat or heating to the human or mammalian body is used to warm up or "loosen-up" joint tissue such as ligaments or tendons prior to use to facilitate an increased range of motion prior to normal or strenuous physical activities.

Other circumstances in which the need for application of cold or heat therapy to the human or mammalian body may arise include post-surgical therapy to reduce pain and swelling and promote healing, as well as in orthopedic therapy, sports medicine therapy and rehabilitation programs and applications. Of particular importance are the areas of athletic injury and subsequent therapy, healing and rehabilitation in humans, and injury and subsequent therapy, healing and rehabilitation in thoroughbred race horses.

The most common method of achieving the desired cooling effect has been application of an ice bag to the desired therapy site. This method has several limitations. Ice bags can be cumbersome to apply, and in the case of animals, for example thoroughbred race horses, may be difficult to maintain on the therapy site. Ice bags can apply uneven cooling to the therapy site, are often difficult to contour to the area of the mammalian body to be treated, and the intensity of cooling is difficult to control. Often the application is either too cold, or not cold enough. A common ice bag has further limitations as well. As the ice melts, an ice bag may leak, causing inconvenience or more serious consequences. Finally, the static application of cold or cooling can become uncomfortable and unpleasant, usually resulting in the subject prematurely terminating the application before the full beneficial affect can be achieved.

A number of variations have been proposed to improve upon the ice bag or pack, but none fully addressed all of its shortcomings. For example, some have been known to use a bag of frozen peas (or other vegetables) as a substitute for an ice bag. The frozen peas allow more uniform cooling of the site, generally contour to the site better than a bag of ice cubes, and apply less severe cooling. Of course, this alternative has a number of drawbacks as well. A bag of frozen peas has limited available cooling capacity, and as with any bag, contouring to a part of the mammalian body such as the human knee can be difficult or impossible, resulting in uneven cold application.

Other variations on the basic ice bag or ice pack include a wrap or strap-on device which holds the source of cooling on the therapy site. These devices generally are designed for use on specific locations on the human body, and generally contour better to the therapy site and are held in place by means of belts or straps. These devices also have several shortcomings, however. Certain types have built-in reservoirs to provide a source of cooling, such as containers of frozen water. These devices must be kept frozen until ready to use, and once their cooling capacity is expired, they must be re-frozen before they can be used again. The intensity of cooling with these wrap or strap-on devices is also difficult to control, and they are capable of applying only static cooling to the site. There are also generally cumbersome, as the source of thermal cooling must be located entirely within the device and held at or on the therapy site.

Also available are chemical cold-packs comprised of two or more chemical substances stored separately in a flexible packet. When needed, the packet is manipulated, causing an internal seal to break and the chemical substances to mix. The substances, when mixed, have an endothermic reaction which causes the packet to cool. While these devices are useful in remote sites and in certain emergency situations, they afford little advantage over the ordinary ice bag. Furthermore, they can generally be used only one time, are of limited cooling capacity or duration, operate at one non adjustable temperature, and are prohibitively expensive for use in a regular cold therapy program.

More recently, a commercially available apparatus for accomplishing the desired cooling of the human knee has been developed which incorporates a cold reservoir consisting of a large cooler. The water within the cooler is circulated by means of a pump which circulates the cooled water from the cooler through a tube to a bladder and back trough a tube to the cooler. The bladder is applied to the therapy site and held in place by means of a wrap or strap device. This apparatus has many advantages over an ice pack or ice wrap. The cooler and source of cooling, generally ice, is held in a container separate from the therapy site. In this type of device, the rate of cooling is adjusted by increasing or decreasing the flow resistance by using a manually operated flow restriction valve or electrically setting the pump speed to a predetermined fixed value.

This apparatus also has several shortcomings. The device is incapable of supplying a measured and controlled cooling temperature to the therapy site, and is incapable of providing tactile stimulation to the therapy site. The device is also cumbersome in that the pump used to circulate the cooling fluid must be manually submerged in the cooler, and there is an ever-present danger of electrical shock due to the proximity of the electrical power cord and the circulating water.

The most common method for achieving the desired heating effect has been through the application of a hot water bottle or steamed towels to an injury site. As with similar cold therapy modalities, this form of heat therapy suffers from the same shortcomings in terms of ease of application and temperature regulation due to a lack of any temperature control mechanism at the injury site.

DESCRIPTION OF THE PRIOR ART

Heretofore, a number of devices and systems have been employed to impose cold with or without pressure on parts of the human or mammalian body. Miller (U.S. Pat. No. 2,531,074 of Nov. 21, 1950) discloses an appliance for a dry massage of a therapy site by water of controlled temperature in a sequence at alternatively high and low pressures applied to a multitude of adjacent chambers of flexible wall material and suggests that the water can be either heated or cooled.

Chessey (U.S. Pat. No. 2,726,658 of Dec. 13, 1955) discloses a system, including a coolant control and supply unit, and a liquid-impervious appliance receiving the coolant and applied as a pad to a body portion of an animal, including a mechanical refrigeration system thermostatically controlled by the temperature of the coolant which is pumped through the appliance.

Grossan (U.S. Pat. No. 3,993,053 of Aug. 5, 1975) discloses a massaging system including a flexible pad having fixed to one face a set of elastic tubing coils forming part of a recirculating hydraulic system, including a pump for creating pulsating fluid flow, and suggests that the pressure and temperature of the circulating liquid may be controlled by the operator.

Copeland, et al. (U.S. Pat. No. 4,149,529 of Sep. 16, 1977) discloses a portable apparatus for controllably cooling and variably applying pressure to a portion of a mammalian body including a liquid supply, control unit, means to circulate the liquid and heat exchanger in the fluid reservoir mounted in a supply unit of sufficient size to support the weight of a human and receive a human limb such that the reservoir may be employed as a whirlpool bath.

Although all the devices described above may be functional and presumably operable, there is a need for an improved apparatus for applying cold or heat to a human or mammalian body which is small enough to be easily transported and used in a wide variety of locations, adaptable to many different mammalian body forms and potential therapy sites, capable of providing controlled temperature therapy at a preset temperature or by a preprogrammed temperature profile, capable of monitoring the therapy temperature directly at the therapy site, and capable of providing tactile stimulation to the therapy site to alleviate the problems of static cooling and enhance the beneficial effects of the cooling therapy. The present invention fulfills these needs, and further provides related advantages.

SUMMARY OF THE INVENTION

The present invention provides an easily transportable apparatus for applying closed-loop temperature controlled cold or heat to a portion of the human or mammalian body. The apparatus comprises an insulated water reservoir within a sturdy housing, covered by a splash-proof lid, and is small enough is be easily situated in any convenient location for cold/heat therapy by the user. Within the reservoir housing but external to the reservoir is contained a self-priming fluid pump with a means of exchanging a measured portion of the re-circulation water with water from the reservoir to maintain the circulation water at a desired temperature. The pump is powered by a small mechanically integrated electric motor. Also contain in this area are the microprocessor-based temperature and pump/heat exchanger control electronics, and internal fluid tubing connections between the pump and the water reservoir, and between the pump and supply line connectors mounted on the housing. User controls and a temperature read-out display are also located on the reservoir housing.

The reservoir in the reservoir housing can accommodate crushed ice, ice cubes or a pre-formed freezable cold source, such as commonly used in portable coolers, and contains enough cooling capacity for generally all therapy applications. The reservoir may be easily recharged with additional ice if needed while therapy is continuing, and without the need for the subject to remove the bladder from the therapy site. For heat therapy, hot water can be introduced into the reservoir or the reservoir fluid can be actively heated by an immersible heater to maintain a constant temperature for controlled heating applications.

The apparatus monitors the therapy temperature and produces an audible signal when the cold or heat source is exhausted and the apparatus is no longer able to maintain the desired therapy temperature within certain preset tolerances.

The fluid supply lines from the pumps are connected to self-sealing, "quick disconnect" connectors, allowing the user to quickly and conveniently attach and detach various bladder types for various therapy applications. The apparatus can also be adapted to support simultaneous use of multiple bladders fluidly connected in series for therapy at multiple sites, as in bilateral surgery applications. Connecting the bladder to the reservoir housing is a pair of fluid supply lines which are terminated at one end by the mating half of the "quick disconnect" connectors mounted in the reservoir housing.

The supply line pair is held together and encapsulated by a layer of insulating material, such as closed-cell polyurethane foam, making the entire tubing assembly water-tight, durable, flexible, and fully insulated to reduce the ambient heat load on the unit and enhance the comfort and ease of use of the therapy apparatus. The supply line assembly may be of various lengths to suit the particular therapy subject and application. The supply line assembly may be permanently affixed to the bladder or attached by means of "quick-disconnect" connectors at its terminal end. Affixed within the supply line assembly is a pair of thermistors or other suitable temperature-sensing devices, one located in each of the pair of fluid supply lines at or near the quick disconnect mounted in the reservoir housing, the output of which is monitored by the control electronics to implement the closed-loop temperature control of the cold or heat therapy.

Various shapes and sizes of bladder are contemplated to accommodate the various therapy subjects, whether human or animal, and the various therapy sites of the mammalian body. All bladders will generally consist of two layers of flexible plastic or other material, completely sealed or welded at the edge or seam, and constructed to allow generous expansion and contraction in response to the varying pressure imposed by the pumps when applying tactile stimulation, and to ensure even distribution of circulation water or other fluid and the subsequent cooling/heating effect on the therapy site.

The bladder is generally held within a mating strap or wrap, depending upon the therapy subject and site. The strap or wrap may be a fabric or rubber type material, such as neoprene rubber, which is secured to the therapy site by means of belts, straps, "Velcro" fasteners. The strap or wrap, when fastened properly, holds the bladder firmly and evenly against the therapy site, while allowing expansion and contraction in response to the pressure fluctuations created by the pump when applying tactile stimulation.

The apparatus maintains temperature control at the therapy site by a controlled dynamic mixing of cold/hot water from the reservoir with the re-circulation water returning from the bladder within the heat exchanger. By using the real-time temperature information generated by the temperature sensing devices, the microprocessor controls the rate of reservoir/recirculation fluid mixing within the heat exchanger. This maintains the circulation water temperature, and thus the injury site bladder temperature. To ensure even temperature distribution at the therapy site or sites, particularly when multiple bladders are used in series, maximum flow rates and delivery pressure is maintained to minimize the difference between outgoing and returning water temperatures regardless of the heat load. To achieve tactile stimulation at the desired therapy temperature, the pump is periodically turned off for a brief interval to allow the pressure within the bladder to return to zero before turning the pump back on. This action causes the bladder to undergo a deflation/inflation cycle which in turn causes a tactile stimulation in the tissue directly in contact with the bladder. The microprocessor-based control electronics and associated operating program operate the pump accordingly to provide maximum flow of circulation fluid and impose periodic pressure variations on the bladder such that the desired temperature control and tactile stimulation are provided at the therapy site.

The present invention provides an important advance in cold/heat therapy of human and other mammalian subjects that improves ease of use and enhances therapy effectiveness. Other features and advantages of the present invention will be apparent from the following more detailed description of the preferred embodiment, taken in conjunction with the accompanying drawings, which illustrates, by way of example, the principles of the invention.

DETAILED DESCRIPTION OF THE PREFERRED EMBODIMENT

Figure 2:
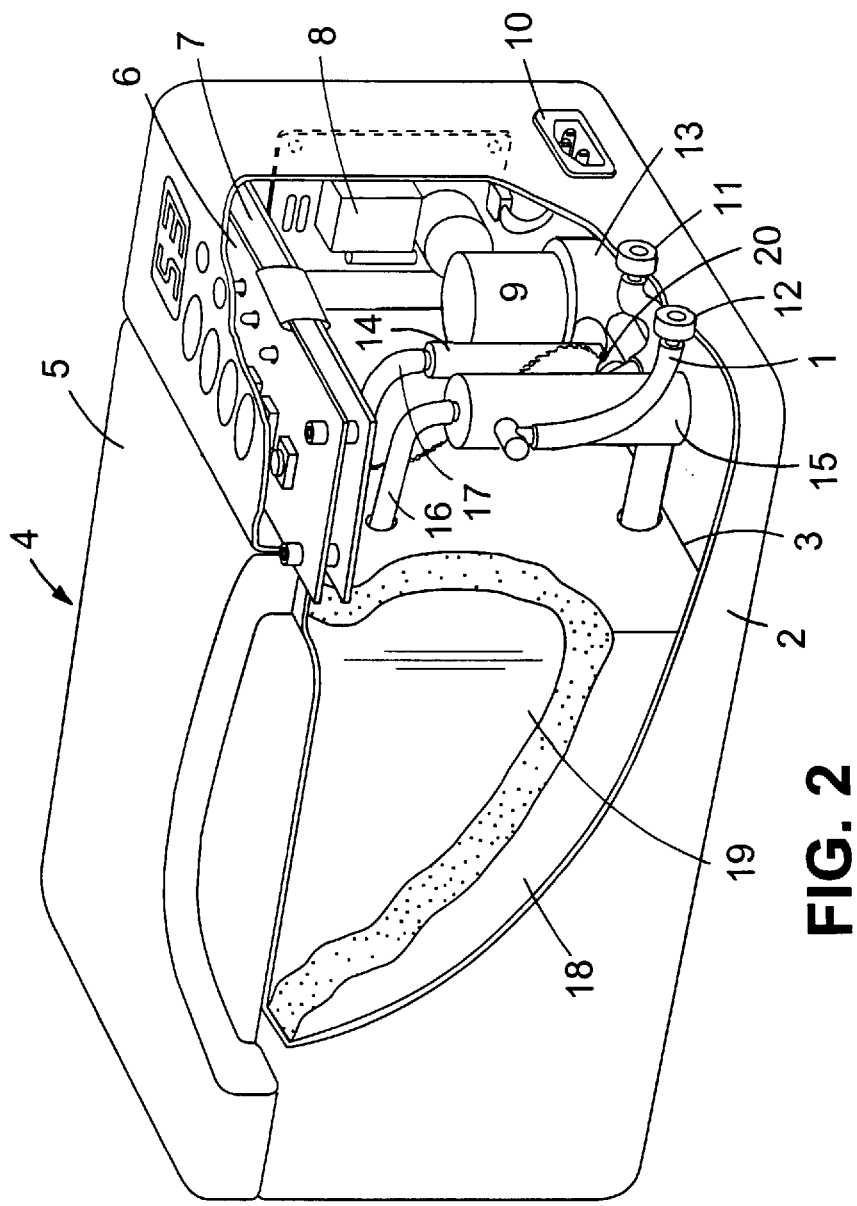
FIG. 2 is a perspective view of the reservoir housing with portions removed or broken away to reveal internal structure.

Referring initially to FIG. 2, there is shown the reservoir housing 4 which includes a protective outer case 2, and inner ice reservoir 19 which is formed within the outer case 2 and open at the top, but otherwise leak-proof. The walls of the reservoir 19 are spaced within and apart from the walls of the outer case 2, the internal space thus formed around the inner reservoir 19 is filled with a thermal insulation 18. The bottom wall 3 of the reservoir 19 is also covered with thermal insulation 18, thus insulating the reservoir 19. The reservoir 19 is covered during operation of the apparatus using a lid 5 which is also thermally insulated and incorporates a seal which fits snugly in the opening of the reservoir 19 to prevent leakage caused by splashing during movement of the apparatus.

The device has pump/heat exchanger 13 that includes an electric-powered fluid pump and a heat exchanger. The fluid pump is connected to micro-processor-based control electronics and an associated operating program. The fluid pump has its fluid input connected to the heat exchanger containing controlled temperature fluid and its fluid output connected by a fluid supply tube to a bladder device. The pump has the capability of pumping fluid from the heat exchanger to the bladder device when operated.

Within the space adjacent to the reservoir 19 and within the outer case 2 are mounted the pump/heat exchanger 13, electric motor 9, microprocessor-based control electronics 7. Pressurized water from the pump/heat exchanger 13 is supplied to the outlet quick disconnect 11 with the return water routed to the air/water separator 15 via the return quick disconnect 12 through return tube 1. To maintain a closed system, air from the priming valve 14 is vented back to the reservoir 19 via vent tube 17, with air vented from the air/water separator 15 via vent tube 16. Closed loop control is affected by two thermistors 20 placed in the supply tube to the outlet quick disconnect 11.

The fluid pump/heat exchanger has its fluid input connected to the reservoir containing cooled/heated fluid and the returning circulation water. The mixing of the reservoir and returning water is controlled by the control electronics to provide output water at a constant selected temperature to the bladder device via the supply tubes.

Electrical power is supplied from a conventional AC wall outlet through power connector 10 and power leads connecting to the switching power supply electronics 8.

Mounted on the reservoir housing 4 are user-operated display/control electronics 6 with push-button controls for user input and a digital display for setting and monitoring therapy temperature and time.

Figure 3:
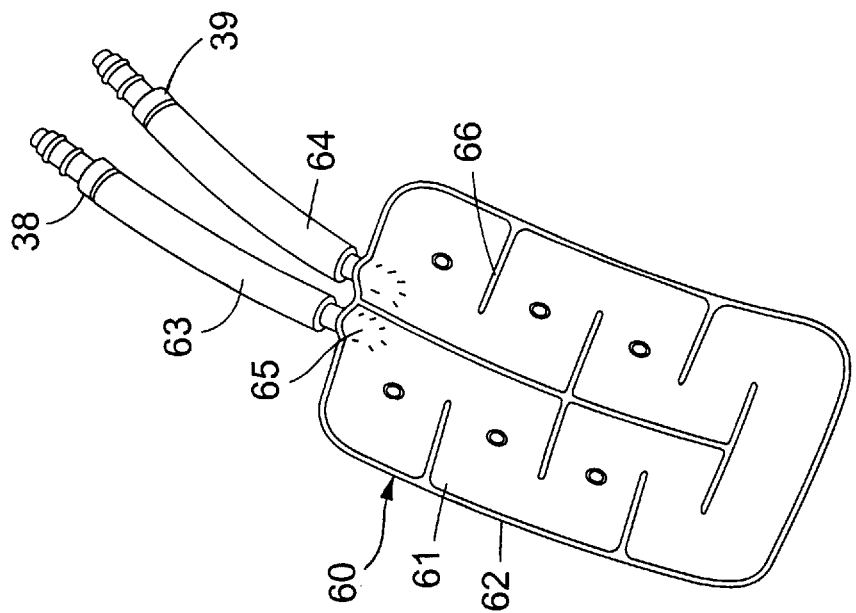
FIG. 3 is a schematic view of the insulated supply lines and bladder showing the internal structure of the bladder.
Figure 3:
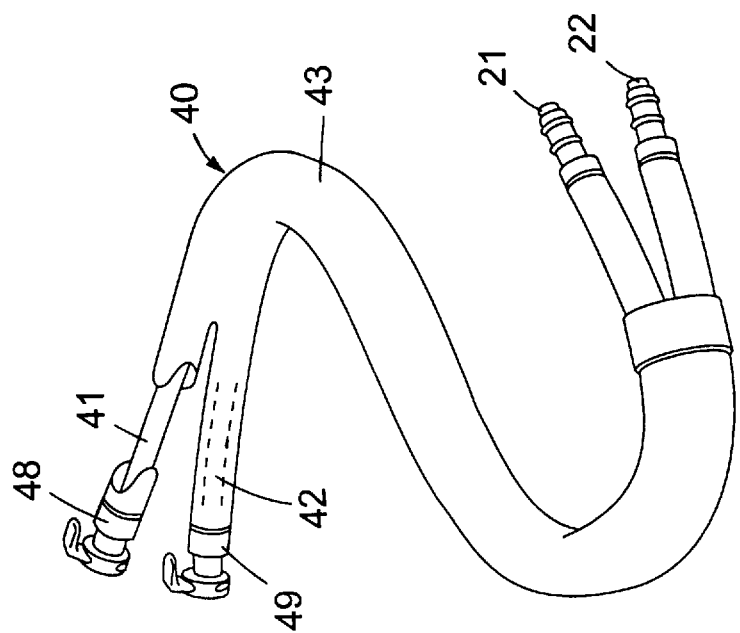

Referring to FIG. 3, the bladder supply line assembly 40 is attached to the reservoir housing 4 by the mating halves of the "quick-disconnect" supply line connectors 21 and 22, connecting a pair of flexible supply tubes 41 and 42 to the internal fluid supply tubes via quick disconnects 11 and 12. The flexible supply tubes 41 and 42 are encased in thermal insulation 43 which reduces ambient heat loads and provides a comfortable means of managing the supply line assembly 40 on the therapy subject. Various lengths for the supply line assembly 40 are contemplated depending upon the particular therapy subject and application.

The supply line assembly 40 may be permanently affixed to the bladder 60 or attached by means of additional "quick-disconnect" supply line connectors 48 and 49.

Figure 4:
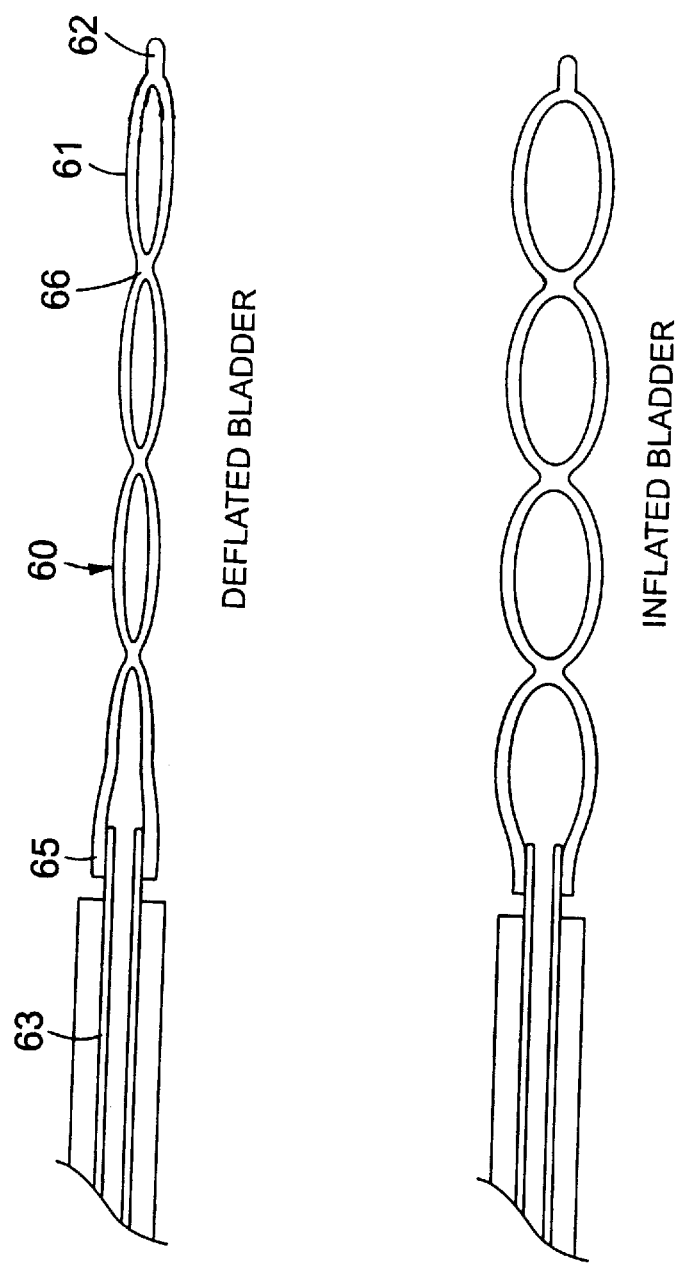
FIG. 4 is a cross-sectional view of a bladder.

Referring to FIG. 3, the bladder 60 may be permanently affixed to the supply line assembly 40 or attached by means of the mating halves of additional "quick-disconnect" supply line connectors 38 and 39. Various bladder shapes and sizes are contemplated for application on specific therapy sites, such as the human knee, ankle, or elbow, to sufficiently surround the therapy site to achieve optimal cold therapy results. The general structure of the bladder 60 is preferably two layers of flexible, weldable polymer or other suitable material 61, which are heat-welded or otherwise sealed completely around the outer seam of the bladder 62. Bladder supply tubes 63 and 64 are attached to the bladder 60 by means of a leak-proof seal 65. The bladder 60 may incorporate one or more internal seams 66 or internal walls (not shown), the function of which is to direct the flow of cooling fluid from the bladder supply tubes 63 and 64 uniformly through the bladder 60, and provide control over expansion of the bladder 60 in response to the higher periodic pressure imposed during tactile stimulation of the therapy site as illustrated in FIG. 4.

Figure 1:
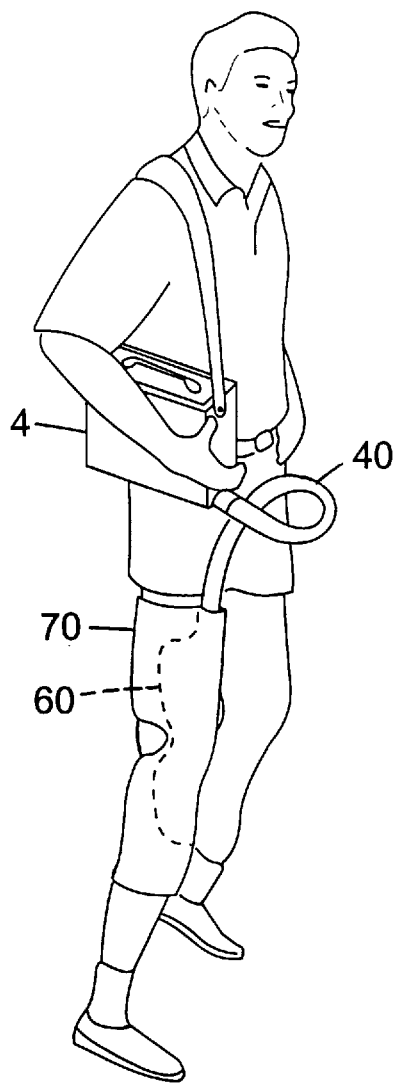
FIG. 1 is a schematic view of the apparatus as typically used by a human subject when applying cold therapy to the knee joint.

Referring to FIG. 1, the bladder 60 is held on the therapy site preferably by means of a wrap 70 made of neoprene rubber or other suitable insulating, flexible material, which is shaped to hold the bladder 60 snugly on the therapy site but allow flexibility for expansion and contraction of the bladder 60 during tactile stimulation of the therapy site. The wrap is held in place preferably by means of "Velcro" fasteners which are attached or sewn onto the wrap 70 such that the wrap 70 can be adjusted by the particular user to fit snugly and comfortably.

The apparatus maintains therapy temperature control at the therapy site by pumping circulation water at a precisely determined temperature from the pump/heat exchanger 13 through the bladder 60 to achieve the desired preset therapy temperature or preprogrammed therapy temperature-time profile, as monitored by the thermistors 20. The reservoir 19, pump/heat exchanger 13, supply tubes 41 and 42, and bladder 60 form a fluid circuit in which fluid may flow in either direction. Net flow through the bladder 60 is achieved by creating a pressurized output flow via the pump/heat exchanger 13 with the spent water returning from the bladder 60 to the air/water separator and ultimately to the inlet side of the pump/heat exchanger 13. The pump/heat exchanger 13, under microprocessor control, continuously displaces a precise amount of re-circulation water with water from the constant temperature reservoir to precisely maintain the temperature of the circulation water exiting the pump/heat exchanger 13. The displaced re-circulation water is returned to the reservoir via the air/water separator 15 to maintain a constant volume in the circulation system. To ensure a uniform temperature distribution at the therapy site or sites, particularly when multiple bladders are used in series in post-bilateral surgery therapy, maximum flow rate and pressure through the circulation system is maintained.

To achieve tactile stimulation when this mode of operation is selected by the user, while maintaining the preset or preprogrammed therapy temperature, the pump/heat exchanger 13 is periodically turned off for preprogrammed intervals to periodically allow the pressure in the bladder 60 to be cycled between zero and maximum. This imposed periodic pressure variation on the bladder 60 will provide tactile stimulation at the therapy site while maintaining the desired therapy temperature through the resulting deflation/inflation cycles in response to the pressure variations.

The control electronics 7 incorporate sufficient non-volatile electronic memory to allow storage, recall and implementation of a plurality of preprogrammed or user-programmed therapy temperature-time profiles, in addition to the operating program of the apparatus. In addition to the plurality of preprogrammed therapy temperature-time profiles contemplated to be provided with the apparatus, user-programming may be accomplished through the keys incorporated into the control/display electronics 6.

The control electronics and associated operating program have the capability of comparing the therapy temperature applied at the therapy site or sites to a constant therapy temperature, or to a time-varying therapy temperature-time profile in real time for purposes of implementing closed-loop therapy temperature control. The control electronics and associated operating program monitor the output of the thermistors and produce an audible signal from a sound emitting device when the temperature detected by the thermistors indicates that the cooling/heating capacity in the reservoir is insufficient to maintain the closed-loop therapy temperature control within a preset temperature tolerance value.

The present invention provides an easily transportable cold therapy apparatus providing closed-loop therapy temperature control and tactile stimulation of the therapy site which may be used by human and mammalian subjects and employed on various therapy sites. Other embodiments within the scope of the invention are feasible. For example, a device with dual pumps capable of bi-directional flow closed-loop temperature control and increased tactile stimulation is feasible. A dual pump device could implement closed-loop temperature control using analog control electronics in the form of a solid state thermostat with the therapy site temperature selected with a mechanically operated device, such as a potentiometer in conjunction with a temperature read-out device. Increased tactile stimulation for a dual pump device could be achieved by engaging both pumps simultaneously, imposing momentary higher pressure on the bladder with no net fluid flow momentarily. Since many changes could be made in the above construction and many apparently widely different embodiments of this invention could be made without departure from the scope thereof, it is intended that all matter contained in the above description or shown in the accompanying drawings shall be interpreted as being illustrative only and not limiting.

We claim:

1. A thermal therapy apparatus for applying temperature-controlled therapy to a therapy site on a mammalian body, comprising:

a therapy pad for applying temperature-controlled therapy to the therapy site;

a recirculation fluid loop comprising a fluid channel defined by said therapy pad;

a pump for circulating fluid through said recirculation fluid loop;

a thermal reservoir for containing fluid;

a fluid exchanger coupling said thermal reservoir with said recirculation fluid loop, said fluid exchanger being constructed to mix a controllable amount of thermal reservoir fluid into said recirculation fluid loop; and a control mechanism coupled to said fluid exchanger for enabling adjustable control of the mixing of thermal reservoir fluid into said recirculation fluid loop to thereby control the temperature of the fluid circulating in said recirculation fluid loop.

2. The therapy apparatus of claim 1, wherein said heat exchanger comprises means for delivering a predetermined volume of fluid from said thermal reservoir into said recirculating fluid loop.

3. The therapy apparatus of claim 1, wherein said therapy pad includes a flexible surface and wherein said control mechanism is coupled to said pump for enabling adjustable control of fluid pressure in said therapy pad.

4. The therapy apparatus of claim 3, wherein said control mechanism is adapted to vary pressure of recirculating fluid within said therapy pad in a manner to apply tactile stimulation to a therapy site by increasing and decreasing fluid pressure in said therapy pad.

5. The therapy apparatus of claim 1, wherein said control mechanism comprises an alarm adapted to actuate whenever said thermal reservoir lacks thermal capacity to maintain a predetermined therapy temperature.

6. The therapy apparatus of claim 1, wherein said recirculating fluid loop comprises a first temperature sensor for monitoring therapy temperature.

7. The therapy apparatus of claim 6, wherein said control mechanism comprises control electronics for said heat exchanger, said control electronics being coupled to said first temperature sensor, user-operated controls and a display for manual selection and visual confirmation of therapy temperature, said control electronics comprising an associated operating program and means for programming, storing and retrieving a therapy temperature-time profile for implementing therapy temperature control.

8. The apparatus of claim 7, wherein said control electronics further comprises means for determining a time-varying therapy temperature specified in said therapy temperature-time profile in real time for implementing therapy temperature control.

9. The apparatus of claim 8, wherein said control electronics further comprises means for comparing time-varying therapy temperature applied at said therapy site to a temperature specified in said therapy temperature-time profile in real time for implementing closed-loop therapy temperature control.

10. The therapy apparatus of claim 7, wherein said control electronics further comprises an alarm for warning a user when said thermal reservoir lacks thermal capacity to maintain therapy temperature.

11. The therapy apparatus of claim 10, wherein said alarm comprises a second temperature sensor connected to said control electronics for monitoring temperature in said recirculating fluid loop of fluid exiting said therapy pad, said first temperature sensor monitoring temperature in said recirculating fluid loop of fluid entering said therapy pad, said control electronics monitoring said first temperature sensor and said second temperature sensor and producing a signal when temperatures detected by said first temperature sensor and said second temperature sensor indicate that said thermal reservoir has insufficient thermal capacity to maintain a selected therapy temperature within a preset tolerance value.

* * * * *

(12) EX PARTE REEXAMINATION CERTIFICATE (8407th)
United States Patent
Kolen et al.

(10) Number: US 5,865,841 C1
(45) Certificate Issued: Jul. 19, 2011

(54) COLD THERAPY APPARATUS

(75) Inventors: Paul T. Kolen, Encinitas, CA (US); Thomas D. Ford, San Diego, CA (US)

(73) Assignee: Credit Suisse, New York, NY (US)

Reexamination Request:
No. 90/011,020, Jun. 30, 2010

Reexamination Certificate for:
Patent No.: 5,865,841
Issued: Feb. 2, 1999
Appl. No.: 08/450,641
Filed: May 25, 1995

(30) Foreign Application Priority Data

Mar. 1, 1995 (IR) .............................................. S950163

(51) Int. Cl.
*A61F 7/00* (2006.01)

(52) U.S. Cl. .......................... 607/104; 607/114; 126/204
(58) Field of Classification Search ................... 607/104
See application file for complete search history.

(56) References Cited

U.S. PATENT DOCUMENTS

| 3,316,732 | A | * | 5/1967 | Burton |
| 4,844,072 | A | * | 7/1989 | French et al. |
| 5,033,136 | A | * | 7/1991 | Elkins |
| 5,476,489 | A | * | 12/1995 | Koewler |
| 6,551,347 | B1 | * | 4/2003 | Elkins |

* cited by examiner

*Primary Examiner* — Beverly M. Flanagan

(57) ABSTRACT

A thermal therapy apparatus for applying temperature controlled therapy to a therapy site on a mammalian body includes a therapy pad for applying a selected therapy temperature to the therapy site, a recirculating fluid loop, including a fluid channel defined by the therapy pad; a thermal reservoir, a heat exchanger coupling the thermal reservoir with the recirculating fluid loop, the heat exchanger including a pump for circulating fluid through the recirculating fluid loop; and a control mechanism coupled to the heat exchanger for enabling adjustable control of therapy temperature. The heat exchanger selectively mixes fluid recirculating in the fluid loop with fluid from the thermal reservoir in an adjustable mixing ratio to achieve the selected therapy temperature in the therapy site.

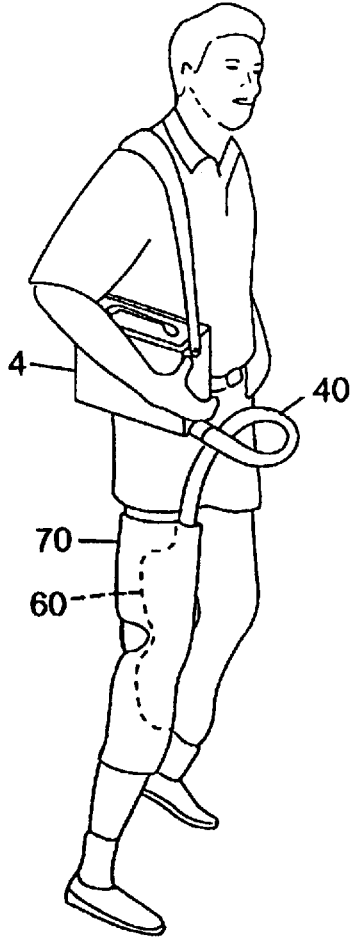

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1-11 is confirmed.

New claims 12-18 are added and determined to be patentable.

*12. The therapy apparatus of claim 1, wherein the reservoir has first walls and second walls, the first walls containing an ice and water mixture and being spaced within and apart from the second walls.*

*13. The therapy apparatus of claim 1, wherein the reservoir contains a sealed lid that can be opened and closed to recharge the reservoir with ice.*

*14. The therapy apparatus of claim 1, wherein the recirculation fluid loop comprises the fluid exchanger, a fluid bladder, a first supply tube that delivers fluid to the bladder and a second supply tube that removes fluid from the bladder and returns it to the fluid exchanger.*

*15. The therapy apparatus of claim 1, wherein the therapy pad comprises neoprene rubber formed as a wrap that is shaped to hold the therapy pad on a patient's limb.*

*16. The therapy apparatus of claim 1, comprising a user-operated display with controls for setting and monitoring therapy temperature.*

*17. The therapy apparatus of claim 1, comprising a microprocessor that controls the fluid exchanger so that it displaces re-circulation water from the therapy pad with water from the reservoir, to maintain the temperature of circulation water delivered to the therapy pad.*

*18. The therapy apparatus of claim 17, wherein recirculation fluid that is displaced by reservoir fluid returns to the reservoir without passing through the therapy pad.*

\* \* \* \* \*